(12) United States Patent
Sato et al.

(10) Patent No.: US 7,933,723 B2
(45) Date of Patent: Apr. 26, 2011

(54) LIVING BODY LIGHT MEASURING DEVICE

(75) Inventors: Hiroki Sato, Fujimino (JP); Atsushi Maki, Fuchu (JP)

(73) Assignee: Hitachi, Ltd., Tokyo (JP)

( * ) Notice: Subject to any disclaimer, the term of this patent is extended or adjusted under 35 U.S.C. 154(b) by 1153 days.

(21) Appl. No.: 11/646,468

(22) Filed: Dec. 28, 2006

(65) Prior Publication Data
US 2007/0208239 A1    Sep. 6, 2007

(30) Foreign Application Priority Data
Mar. 3, 2006   (JP) .................. 2006-057090

(51) Int. Cl.
*G01N 31/00* (2006.01)
(52) U.S. Cl. .......................................... 702/32
(58) Field of Classification Search ............. 702/32; 600/328
See application file for complete search history.

(56) References Cited

U.S. PATENT DOCUMENTS

| | | | |
|---|---|---|---|
| 6,907,279 B2 * | 6/2005 | Sato et al. ........... | 600/322 |
| 2004/0039267 A1 | 2/2004 | Kawasaki et al. | |
| 2004/0127784 A1 | 7/2004 | Yamashita et al. | |
| 2004/0254475 A1 | 12/2004 | Maki et al. | |
| 2006/0006343 A1 | 1/2006 | Tanaka et al. | |
| 2008/0040049 A1 | 2/2008 | Sato et al. | |

FOREIGN PATENT DOCUMENTS

| | | |
|---|---|---|
| CN | 1718154 A | 1/2005 |
| EP | 1 327 418 A1 | 10/2001 |
| WO | WO 2005/120349 A1 | 6/2005 |

OTHER PUBLICATIONS

Maki, A. et al., "Spatial and temporal analysis of human motor activity using noninvasive NIR topography", Medical Physics, vol. 22 No. 12, pp. 1997-2005, Dec. 1995.
Peña, M. et al., "Sounds and silence: an optical topography study of language recognition at birth", PNAS, vol. 100 No. 20, pp. 11702-11705, Sep. 30, 2003.
Taga, G. et al, "Brain imaging in awake infants by near-infrared optical topography", PNAS, vol, 100 No. 19, pp. 10722-10727, Sep. 16, 2003.

* cited by examiner

*Primary Examiner* — Drew A Dunn
*Assistant Examiner* — Stephen J Cherry
(74) *Attorney, Agent, or Firm* — Stites & Harbison PLLC; Juan Carlos A. Marquez, Esq.

(57) ABSTRACT

At each of measurement sites, changes in plural biological data (such as an oxy-Hb signal species and a deoxy-Hb signal species) in a predetermined period are statistically tested independently of each other. By combining results of the plural biological data, the measurement sites are each classified into one out of plural categories. The classified results are each displayed in a single chart. Effective is also a method of setting different activity periods correspondingly to plural Hb signal species, deciding whether or not each of the signal species shows activity or estimating the strength of the signal species, and displaying classification results based on combination of activities of the plural Hb signal species in a single chart. A living body light measuring device using the brain activity analyzing method and displaying method of the invention makes it possible to detect sites where brain activity is generated with a high precision.

16 Claims, 10 Drawing Sheets

LIVING BODY LIGHT MEASURING DEVICE

CLAIM OF PRIORITY

The present application claims priority from Japanese application JP 2006-057090 filed on Mar. 3, 2006, the content of which is hereby incorporated by reference into this application.

FIELD OF THE INVENTION

The present invention relates to a living body light measuring device for measuring data, in particular, signals, inside a living body based on a change in the concentration of an optical absorption material by use of light, and in particular to a living body light measuring device for making brain activity visible by use of data obtained in measurement of living body light.

BACKGROUND OF THE INVENTION

Light that has an optical intensity peak within in a range from the range of visible rays to that of near infrared rays has a high transparency to living bodies. This light can be used to measure data in a living body without attacking the body. This is based on Lambert-Beer's law which teaches that the logarithm value of a measured signal of light is in proportion to the path length of the light and the concentration thereof. This law has been developed. Additionally, a technique for measuring a signal representing a relative change in the concentration of hemoglobin (Hb) (hereinafter "an Hb signal") in a living body has been developed. The Hb signal that can be measured by the present technique is generally classified into the following three species: an oxidized Hb ("oxy-Hb") signal, a deoxidized Hb ("deoxy-Hb") signal and a total signal of oxy-Hb and deoxy-Hb ("total-Hb signal"), which are called an "oxy-Hb signal (species)", a "deoxy-Hb signal (species)" and a "total-Hb signal (species)", respectively.

Maki A et al., (1995) "Spatial and temporal analysis of human motor activity using noninvasive NIR topography", Medical Physics 22, 1997-2005) suggests a technique for measuring Hb signal values of multi-points in the cerebral cortex of a human being simultaneously without attacking the cortex, and this technique has been spreading in research and clinical medicine. The document discloses a method of measuring Hb signal values of the cerebral cortex, thereby measuring brain functions of a human being. Specifically, as the perception mechanism or motor function of a human being is active, the blood flow in the field taking charge of the function inside the cerebral cortex increases. Thus, an oxy-Hb signal species or deoxy-Hb signal species in the field changes. Accordingly, the activity situation of the brain can be evaluated. Typical examples of the change accompanying the brain activity are an increase in an oxy-Hb signal species and a decrease in a deoxy-Hb signal species. These changes are caused by an increase in the blood flow to supplement oxygen and glucose, which are consumed for metabolic activity accompanying neural activity. The increasing blood is arterial and contains oxygen. The increase is far more, as compared with oxygen consumption. It appears that this results in an increase in the oxy-Hb signal species and a decrease in the deoxy-Hb signal species. In general, the increase in an oxy-Hb signal species is more than the decrease in a deoxy-Hb signal species. Therefore, the total-Hb signal species, which is the total of, the oxy-Hb signal species and the deoxy-Hb signal species, increases. It is known that these blood flow changes are generally delayed by about 5 to 7 seconds from neural activity. This technique is beneficial because it allows a subject's brain function to be measured without attacking the subject's brain nor excessively restricting the subject. One beneficial use of this technique is that it can realize the measurement of brain functions of healthy newborns or infants, which has not yet been realized hitherto. Pena M et al. (2003) "Sound and silence: an optical topography study of language recognition at birth", Proc Natl Acad Sci USA 100(20), 11702-11705; and Taga, G et al. (2003), "Brain imaging in awake infants by near-infrared optical topography", Proc Natl Acad Sci USA 100(19), 10722-10727).

According to the present technique, three species of an Hb signal, that is, an oxy-Hb signal species, a deoxy-Hb signal species, and a total-Hb signal species can be measured. However, in conventional research on brain functions, there are hardly examples wherein these plural signal species are effectively used. For example, in Maki, et al., which teaches measuring the activity of an adult's motor area, describes a change in the three species of an Hb signal with the passage of time; however, without referring to a difference therebetween substantially, attention is paid to only an increase in the total Hb signal species and his/her brain activity is evaluated. In the same manner, in Pena et al., attention is paid to only an increase in a total Hb signal species and brain activity is evaluated. On the other hand, Taga et al. indicates both of an oxy-Hb signal species and a deoxy-Hb signal species. However, no useful information is extracted from a difference therebetween. For example, from a difference between activity waveforms, it is stated that a decrease in the deoxy-Hb signal species is slower and smaller than an increase in the corresponding oxy-Hb signal species. However, analysis based on the attention of the difference is not made. In past research, including Taga et al., consistency is lacking in the results for a deoxy-Hb signal species than in those of the corresponding oxy-Hb signal species, the activity of which is clearly shown; therefore, about the deoxy-Hb signal species, only a matter that the signal-to-noise ratio thereof is low is studied in many cases. This fact is based on a presupposition that an oxy-Hb signal species and the corresponding deoxy-Hb signal species originally indicate the same brain activity. As described above, in spite of the existence of the technique capable of measuring the three species of an Hb signal, there has not been any method of using a difference or a common facture therebetween to improve the detection precision of brain activity.

SUMMARY OF THE INVENTION

In living body light measuring device wherein Hb signal species are measured at plural sites, and brain activity is made visible, a method for indicating sites of brain activity precisely is essential. However, in the prior art, there is not any collective opinion about an effective method for selecting one or more species to be used from the three Hb signal species nor an effective method for displaying the selected species. Thus, it is difficult to show the central site of brain activity evidently from data from plural measurement sites. In a main conventional method, only one out of the three Hb signal species is used in order to make spatial sites of brain activity visible from data from plural measurement sites, and the intensity of the signal species, which has a unit of millimole millimeter (mM·mm), is represented by use of colors or the like. In this way, for the individual measurement sites, the signal intensities are mapped. However, some measurers evaluate brain activity by use of only the oxy-Hb signal species while other measurers evaluate it by use of only the total Hb signal species. In such a manner, under the present circumferences, Hb signal species to be investigated are different in accordance with measurers. Thus, no collective option has been obtained as whether or not a difference is generated in an obtained brain activity map, dependently on the used Hb signal species; or the Hb signal species to be used to evaluate the activity.

With regard to living body light measuring devices measuring Hb signals at plural sites to make the activity of a brain visible, an important theme is the development of an analyzing method and a displaying method for identifying sites where the brain activity is generated more precisely in a more standardized manner.

The inventors have used a living body light measuring device as described above to measure brain activity of a subject where plural measurement points are arranged in the whole of the brain of the subject. Thus, the inventors have analyzed each of the obtained Hb signal species (an oxy-Hb signal species and a deoxy-Hb signal species) statistically, and displayed the measurement points where a significant change is caused (the points where each of the signal species is tested by a predetermined analyzing method so that a change which is caused only at a predetermined possibility or less is generated) as activity sites, thereby finding out the following: an active site distribution of the oxy-Hb signal species and that of the deoxy-Hb signal species are somewhat different from each other; however, the activities of both of the Hb signal species overlap with each other at some of the measurement points (see a display section 101 in FIG. 1).

In FIG. 1, brain activity is evaluated by use of the oxy-Hb signal species and the deoxy-Hb signal species. The measurement points where only the oxy-Hb signal species is active (increased) are each represented by a lattice pattern, the measurement points where only the deoxy-Hb signal species is active (decreased) are each represented by a dot pattern, and the measurement points where both of the oxy-Hb signal species and the deoxy-Hb signal species are active are each represented by a black solid. Sites where the activities of the plural Hb signal species overlap with each other are consistent with activity sites presumed from given stimulations. More localized activity sites, which cannot be identified by use of only an activity map of only one out of the Hb signal species, are shown. From this finding, the present invention suggests a method of: testing, independently and statistically, changes in plural biological data (an oxy-Hb signal species, a deoxy-Hb signal species, and so on) at measurement points in a predetermined period; combining results of the plural biological data; classifying each of the measurement points into one out of predetermined categories; and displaying the classified results in a single chart. This invention makes it possible to detect more localized brain activity sites with high precision.

About the activity of an Hb signal as described above, the spatial spread of the activity and the time required until the activity reaches a peak are each varied in accordance with the species of the Hb signal (the oxy-Hb signal species or the deoxy-Hb signal species) (FIG. 2). FIG. 2 shows an example wherein brain activity generated from a sound stimulation is analyzed at intervals of 2.5 seconds from the time when the stimulation begins to be given, and the results are shown.

In the same manner as in FIG. 1, each of the Hb signal species is statistically analyzed, and the brain activity is displayed in a state where the activity is classified into three cases (the case that only the oxy-Hb signal species is active, the case that only the deoxy-Hb signal species is active, and the case that both of the oxy-Hb signal species and the deoxy-Hb signal species are active). Measurement points where the oxy-Hb signal species increases make their appearances after 2.6 to 5.0 seconds from the time when the stimulations begin to be given. The number of such measurement points becomes largest in 7.6 to 12.5 seconds from the time when the stimulation begins to be given. On the other hand, measurement points where the deoxy-Hb signal species decreases begin to make their appearance after 7.6 to 10.0 seconds from the time when the stimulation begins to be given. The number of such measurement points becomes largest in 10.1 to 15.0 seconds from the time when the stimulation begins to be given. As described herein, the period when the activity of an Hb signal can be most remarkably detected is varied in accordance with the species of the Hb signal. Therefore, brain activity sites can be identified with a higher precision by setting an activity period varied in accordance with the species of the Hb signal, evaluating the existence or non-existence of activity or the intensity thereof, and displaying the classification where the activities of the plural Hb signal species are combined in a single chart (FIG. 3).

In short, sites of brain activity and the period thereof can be analyzed and displayed with a high precision by means of a living body light measuring device for measuring brain function, comprising: plural light-radiating means from which light is radiated to the head of a subject, plural light-receiving means for detecting transmitted light which is transmitted through the head of the subject after being radiated from the light-radiating means, a calculating section for calculating a change in the concentration of oxidized hemoglobin and a change in the concentration of deoxidized hemoglobin in the head of the subject at a measurement point where measurement is made by means of a pair of each of the plural light-radiating means and the corresponding light-receiving means on the basis of a signal detected by the light-receiving means, and a display section for displaying calculation results obtained by the calculating section, wherein the calculating section decides whether or not the oxidized hemoglobin concentration change and the deoxidized hemoglobin concentration change are each significant at each of the measurement points, and the display section displays results of the decisions about the individual measurement points.

The living body light measuring method of the present invention, using the above-mentioned brain activity analyzing method and displaying method, makes it possible to detect sites where brain activity is generated with a higher precision than methods in the prior art. Furthermore, the state of blood circulation which accompanies brain activity can be evaluated in more detail by visualizing differences in time and spatial spread between the activity of an oxy-Hb signal species and that of a deoxy-Hb signal species, as shown in FIG. 2.

DETAILED DESCRIPTION OF THE PREFERRED EMBODIMENTS

Figure 1:
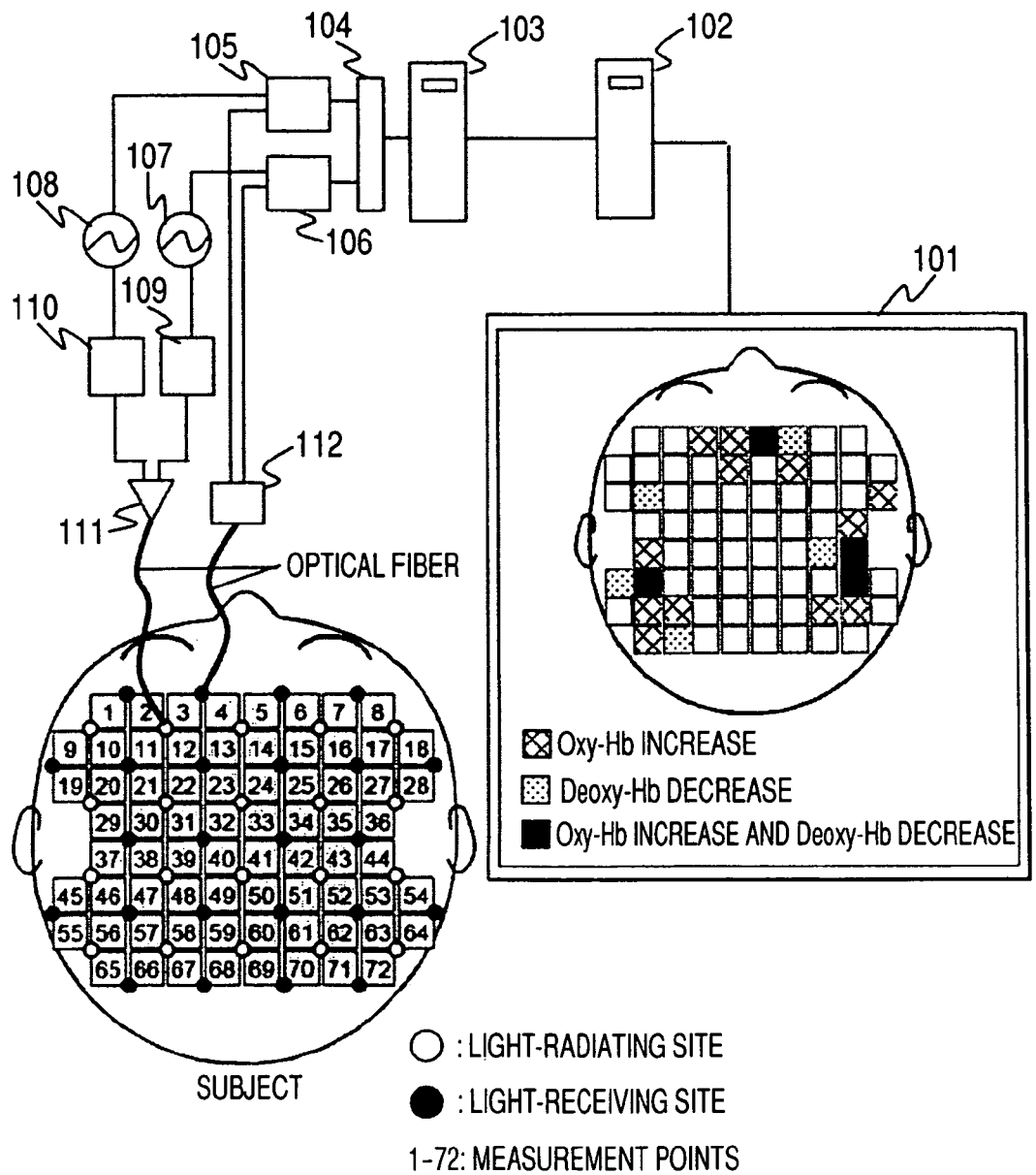
FIG. 1 is a view showing structural blocks of a device of an embodiment of the invention and a display example of brain activity based on individual Hb signal species and a combination thereof.

With reference to FIG. 1, a basic embodiment for carrying out the present invention will be described hereinafter. FIG. 1 is a block diagram illustrating an outline of a living body light measuring device according to the invention. Its living body light measuring section has: a control unit 103 made of a computer, typical example of which includes a personal computer and a work station; two laser diodes 109 and 110 which show peak wavelengths at different peak wavelengths; oscillators 107 and 108 for generating signals for modulating the two laser diodes with different frequencies; an optical mixer 111 for mixing the two light rays, the peak wavelengths of which are different from each other; a light radiator for radiating light from the optical mixer 111 to a light radiating site on a subject through an optical fiber; an optical detector 112 for detecting the mixed light at a light detecting site which is appropriately apart from the light radiator (a site about 3 cm apart therefrom in the present example); lock-in amplifiers 105 and 106 wherein modulated frequencies from the oscillators are inputted as reference signals; and an analog-digital converter 104 for converting transmitted light signals of light rays having individual wavelength bands, which are outputs of the lock-in amplifiers, from analogue signals to digital signals. The substantially middle point between the light radiating site and the light detecting site is rendered the center of a site to be measured. In FIG. 1, only about a measurement site 3, a structure wherein the site is connected to the device is precisely illustrated. Actually, however, all of light radiating sites and light detecting sites illustrated in FIG. 1 are connected to the device through optical fibers. In the device, the oscillators are used to separate plural signals; therefore, optical signals from plural sites can be detected by means of the single detector. In the present example, the oscillators are used to separate plural signals in this way; however, optical signals can be separated at a lighting-on timing by use of pulse light without using any oscillator. Transmitted light signals of light rays having individual wavelength bands are analogue-digital-converted at the analogue-digital converter 104, and then inputted and memorized in the control unit 103. In the control unit 103, on the basis of the transmitted signals, individual Hb signal species in each of sites to be measured are calculated out. The calculated-out signals are forwarded and memorized into a data analyzing unit 102, together with the original signals (the transmitted signals). The method for calculating out the Hb signal species from the transmitted light signals is described in detail in Maki. In the present example, the control unit 103 and the analyzing unit 102 are separately described and illustrated. However, both of the functions thereof can be attained by means of a single PC.

In the analyzing unit 102, each of the measured Hb signal species is statistically analyzed to decide whether or not the signal shows a significant activity. Typical examples of a method for the statistical analysis in this case include t test and dispersion analysis. In ordinary brain activity measurements, a reaction generated when a specific stimulation or theme is given to a subject is compared with his/her state in a rest period, and then the result from the comparison is grasped as a brain activity. Consequently, comparison between signals in a rest period and signals in a period when a reaction based on a stimulation or theme may be generated (an activity period) is a basis of the statistic analysis. Typical examples of a statistic method for making this comparison include t test, F test, dispersion analysis, and multiply comparison. Additionally, not only a parametric test but also a non-parametric test can be used. Additionally, the following methods can be used: a method of giving different stimulations or themes to a subject, and then comparing signals in periods for different activities generated therefrom directly with each other; and a method of assuming a signal waveform indicating an activity responding to some stimulation or theme, and then evaluating similarity of an actual signal waveform to the assumed signal waveform by use of a correlation coefficient or the like. In general, it is known that changes in an Hb signal which accompany brain activity are classified into an increase in an oxy-Hb signal species, a decrease in a deoxy-Hb signal species; and an increase in a total-Hb signal species. In the present example, therefore, these three changes are defined as activity signals. At each of the measurement sites, t test is used to test whether or not each of the three Hb signal species shows activity. The results of the test are displayed in a display section 101. In the measurement of the present example, the following is defined as one block: a sequence of the supply of a sound stimulation for 10 seconds after a rest period having a length set at will within a period from 20 to 30 seconds. This block is repeated 5 times. First, in each of the blocks, a period from 5 seconds after the start of the stimulation to 10 seconds after the end of the stimulation is regarded as an activity period, and the average of signal strengths in the activity period is obtained as an activity value (or the maximum value of signal strengths in the period may be used as an activity value). Moreover, in each of the blocks, the average of signal strengths in a rest period, which is for 5 seconds immediately before the start of the stimulation, is obtained as a rest value. In order to decide whether or not there is a difference between the activity value and the rest value, t test is performed using the average and deviation obtained from the activity values of the five blocks and the average and deviation obtained from the rest values of the five blocks. The wording "t test" is a generic term of statistical testing methods using a matter that statistics follow t distribution in the case of assuming that the null hypothesis is right. The test is a parametric testing method wherein it is assumed that a population follows normal distribution. In the test, the distribution is dependent of the degree of freedom and not on the original average or the standard deviation. This test is used, for example, for testing whether or not there is a significant difference between individual averages of two groups. In the present example, the null hypothesis formulated is that "the average of the rest values is equal to that of the activity values." Then it is tested whether or not a difference is generated between the average of the activity values and that of the rest values. In other words, when the null hypothesis can be rejected at a possibility of, for example, 95% or more, the measured activity is regarded as a significant activity. When an increase in an oxy-Hb signal species or a decrease in a deoxy-Hb signal species is recognized at a possibility that is larger than a certain threshold value, it is decided that brain activity is generated.

The decision as to whether or not a significant activity is generated may depend on a standard that is set by a measurer. The standard may be, for example, whether or not the value of brain activity exceeds a threshold value that is set in a setting-up section by a measurer or it may be a time required until brain activity becomes a maximum value.

The standard for the decision as to whether or not a significant activity is generated may be set for each of the measurement sites. In FIG. 1, the measurement points where only the oxy-Hb signal species is active (increases) are each represented by a lattice pattern, the measurement points where only the deoxy-Hb signal species is active (decreases) are each represented by a dot pattern, and the measurement points where both of the oxy-Hb signal species and the deoxy-Hb signal species are active are each represented by a black solid. Sites where the activities of the two Hb signal species overlap with each other are represented as more localized activity sites. These activity sites are observed in the right and left temporal regions, which correspond to the vicinities of the auditory area, which is expected to react to a sound stimulation. Since a language sound is used, activity is observed in the frontal region also, which is generally thought to be associated with memory or concentration. In this manner, the sites where the activities of the two Hb signal species overlap with each other are satisfactorily consistent with activity sites predicted from the given stimulation. Thus, brain activity sites can be detected with a higher precision therefrom than from an activity map of only one out of the plural Hb signal species.

Figure 2:
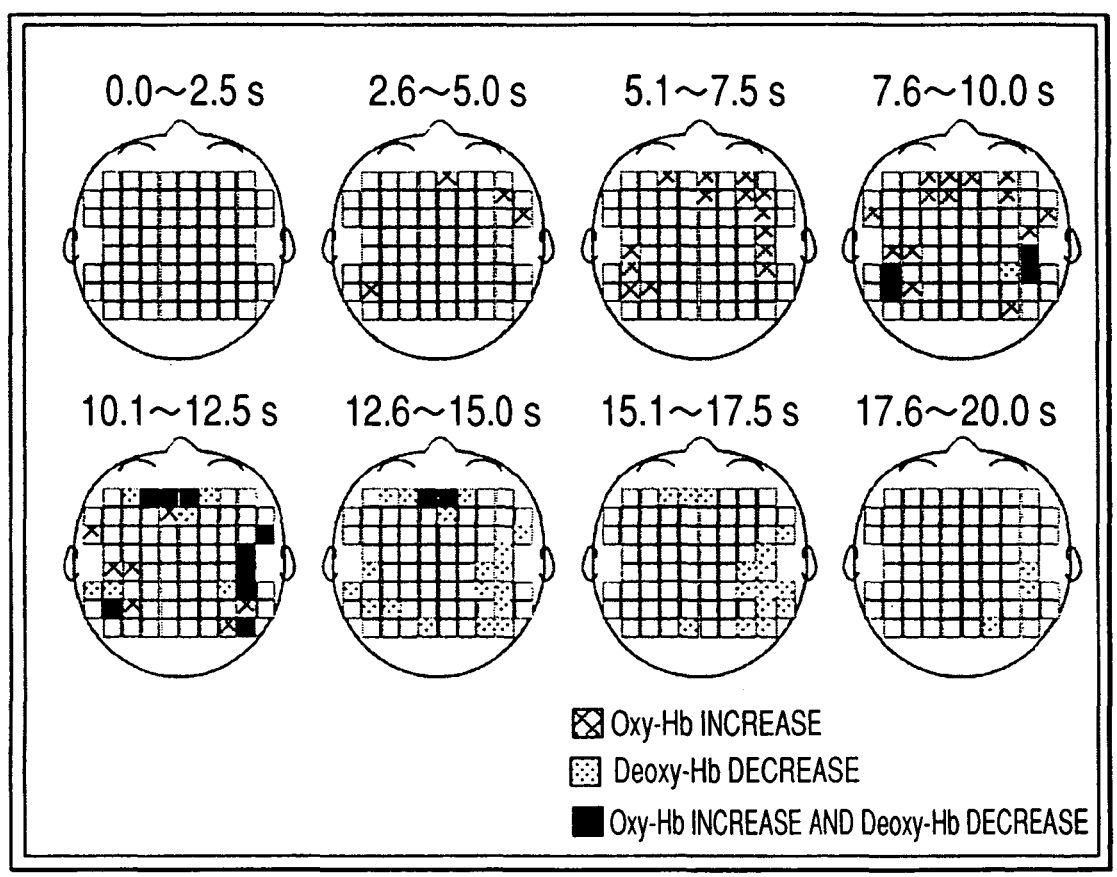
FIG. 2 is a view showing an example wherein activity results of each Hb signal species which are investigated at intervals of 2.5 seconds from the start of a stimulation are displayed.

Furthermore, FIG. 2 shows an example wherein a time window representing an activity period is set for the above-mentioned data at intervals of 2.5 seconds from the start of the stimulation, and the results of activity are analyzed and displayed. In the same manner as in FIG. 1, statistical analysis is made for each of plural Hb signal species. The activity is classified into three cases (1) the case where only the oxy-Hb signal species is active; 2) the case where only the deoxy-Hb signal species is active; and 3) the case where both the oxy-Hb signal species and the deoxy-Hb signal species are active) and then displayed. Measurement points where the oxy-Hb signal species increases begin to make their appearances 2.6 to 5.0 seconds after the start of the stimulation. The number of such measurement points becomes largest in the time windows from 7.6 to 12.5 seconds. On the other hand, measurement points where the deoxy-Hb signal species decreases begin to make their appearances 7.6 to 10.0 seconds after the start of the stimulation. The number of such measurement points becomes largest in the time windows from 10.1 to 15.0 seconds. As described herein, it can be understood that depending on the species of an Hb signal, the spatial spread of activity of the Hb signal or the time required until the activity reaches a peak is varied. In other words, depending on the species of an Hb signal, the time window wherein brain activity can be more remarkably detected is varied. Accordingly, depending on the species of an Hb signal, a varied activity period (time window) is set, and then it is decided whether or not activity of the Hb signal is generated, or the strength of the activity is evaluated. Thereafter, in a single chart, the above-mentioned classification, wherein activities of the plural species of the Hb signal are combined, is displayed, thereby making it possible to identify brain activity sites with high precision.

Figure 3:
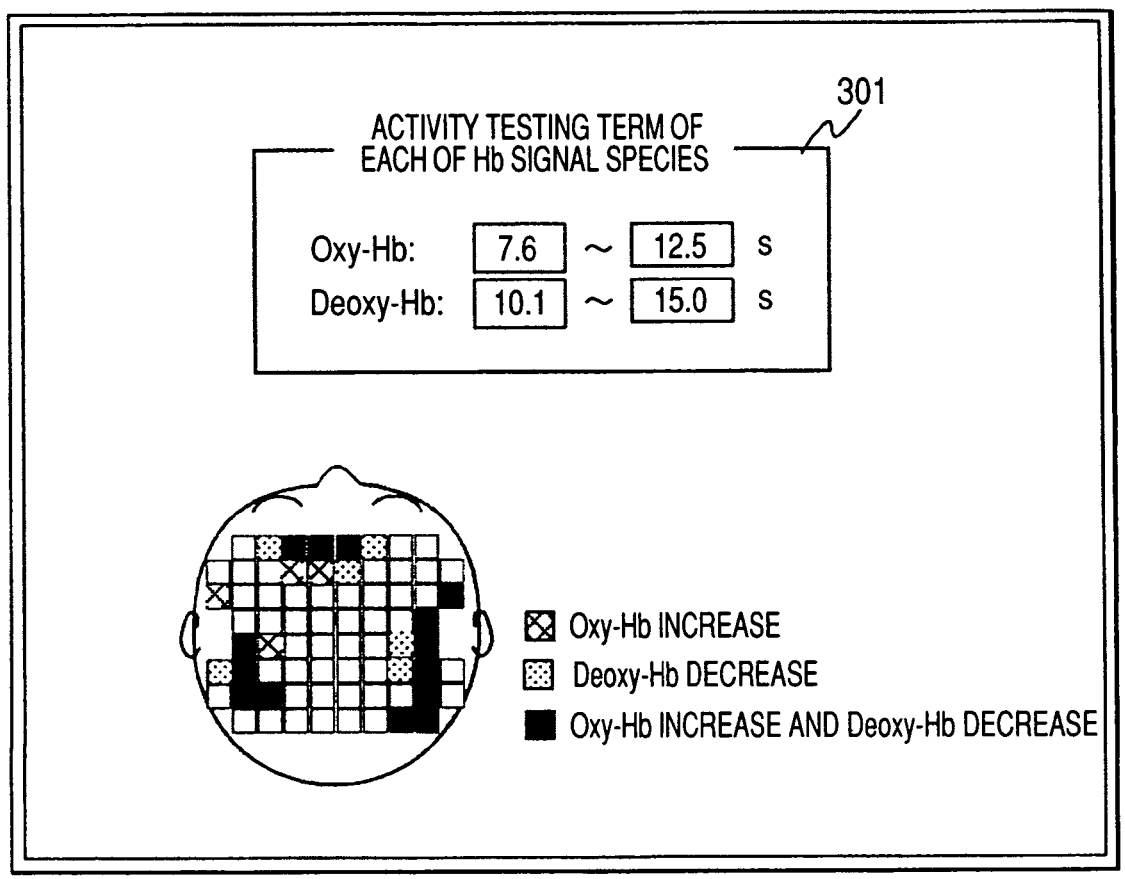
FIG. 3 is a view showing a setting-up section for setting a time window for testing activity of each Hb signal species and a screen wherein a situation of brain activity that is the result of the test is displayed.

FIG. 3 shows an example wherein a period from 7.6 to 12.5 seconds after the start of a stimulation and a period from 10.1 to 15.0 seconds after the start of the stimulation are set into a time window representing an activity period of an oxy-Hb signal species and a time window representing an activity period of a deoxy-Hb signal species, respectively. Brain activity is then analyzed and results of the analysis are represented in a single chart. In the case of disposing a setting-up section 301 capable of setting time windows for representing activity periods varied by the Hb signal species in this way, it is possible to display a more precise activity region, which cannot be detected when a constantly-specified time window is set for all of the activity periods.

Figure 4:
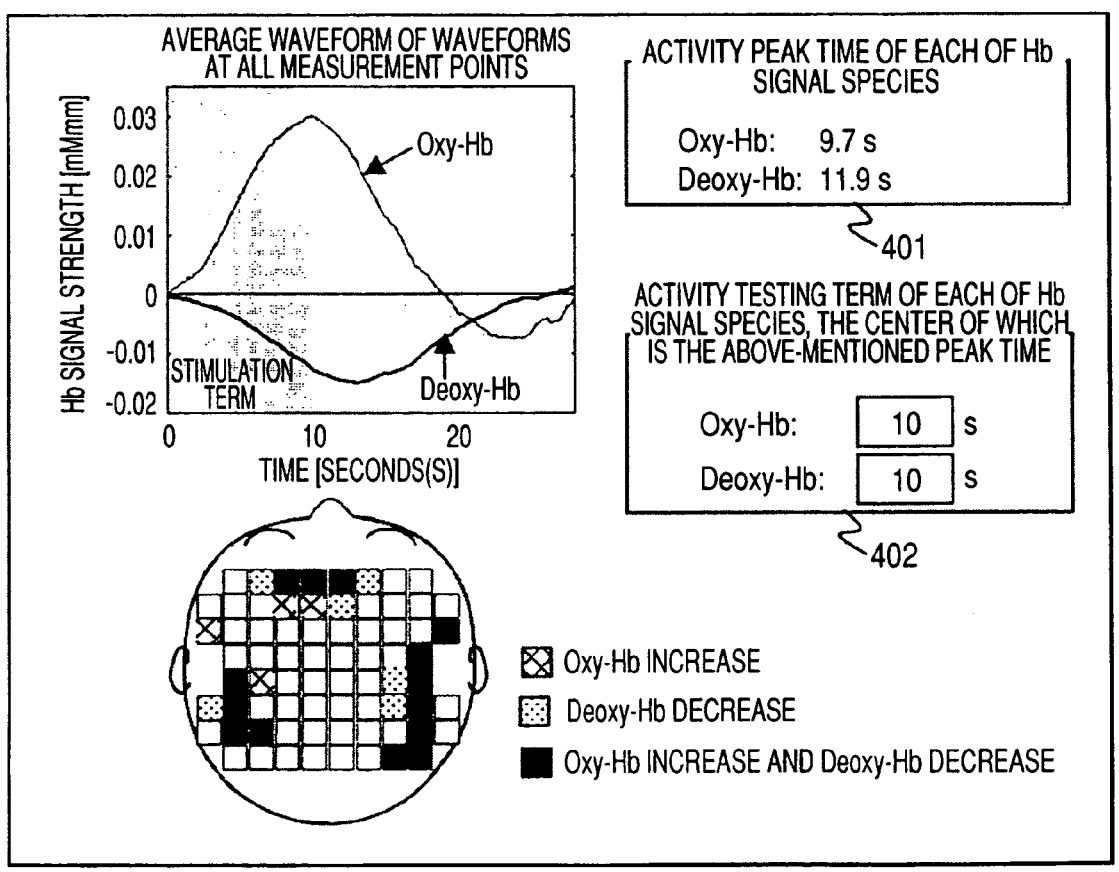
FIG. 4 is a view showing the average waveform of waveforms at all measurement sites, a time up to arrival at an activity peak of each Hb signal species, a setting-up section for setting up a period for testing activity the center of which is at the time of the activity peak, and a screen wherein the brain activity that is the result of the test is displayed.
Figure 5:
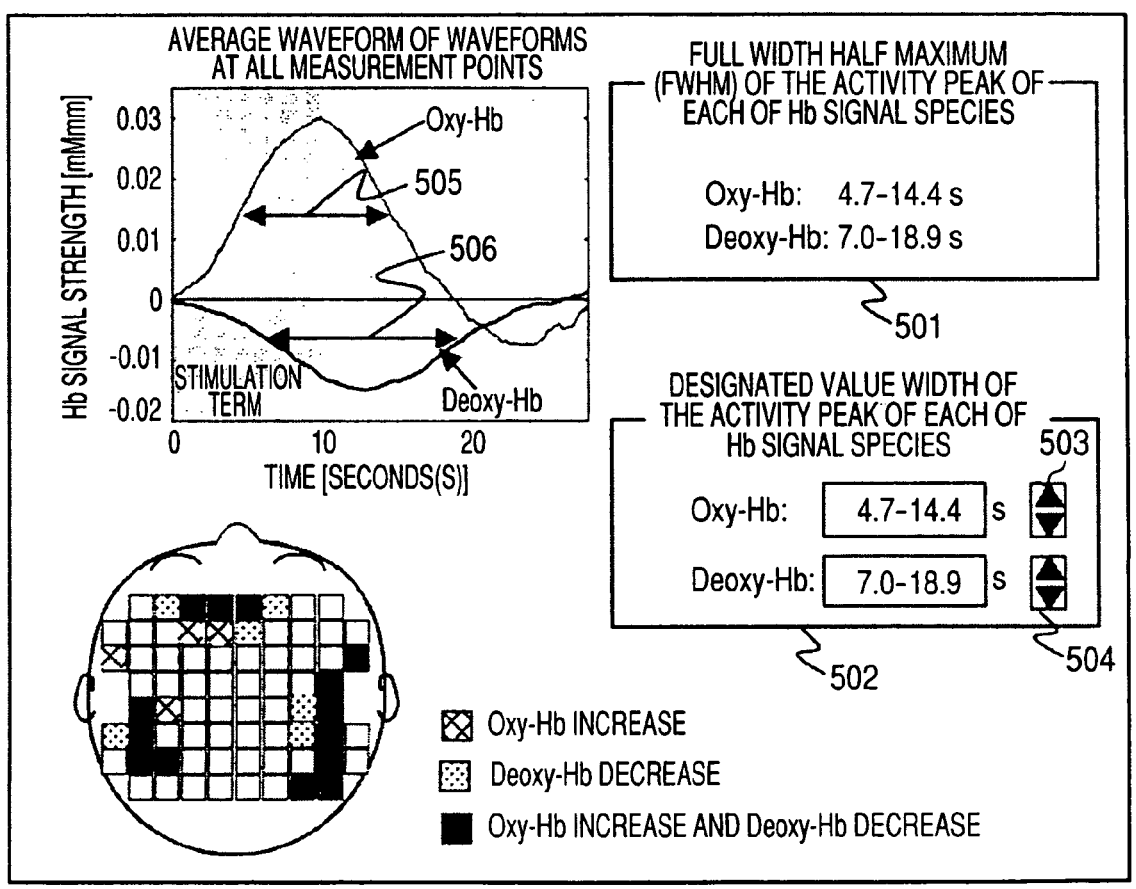
FIG. 5 is a view showing the average waveform of waveforms at all measurement sites, the full width half maximum of an activity peak of each Hb signal species, a setting-up section for setting up a time window the center of which is at the time of the activity peak, and a screen wherein a situation of brain activity that is the result of a test of the Hb signal species is displayed.

FIGS. 4 and 5 show a means for setting a time window representing an activity period of each of plural Hb signal species on the basis of an activity waveform of each of the Hb signal species in order to detect brain activity with a higher precision. FIG. 4 shows a displaying means having a display section 401 for displaying an activity peak of each of the Hb signal species, the peak being calculated from the average waveform of signals of each of the Hb signal species at all measurement points; and a setting-up section 402 for setting up a time window for an activity period, the center of which is the activity peak. A user can decide the time window for the activity period by referring to an average waveform and so forth. In particular, the displaying allows for time windows of an activity period for different Hb species, such as oxy-Hb signal and deoxy-Hb signal species, to be set up independently of each other.

In FIG. 5, shown is a displaying means having a display section 501 for displaying the full width half maximum (FWHM) of an activity peak of each of the Hb signal species, the FWHM being calculated from the average of signal waveforms of each of the Hb signal species at all measurement points; and a setting-up section 502 for setting up a time window showing not less than a reference value the center of which is the activity peak of each of the Hb signal species. The method, used in this case, for setting up the time window is a method of operating arrow bottoms 503 and 504, thereby changing the reference value for each of the oxy-Hb signal species and the deoxy-Hb signal species to set a time window. For displaying the reference values more understandably in this case, effective is a displaying method of moving arrows 505 and 506 for showing the time windows up and down by operating the arrow buttons 503 and 504, respectively. Of course, in order to set the reference values, it is allowable to use a method of inputting selected values directly, or a method of inputting a ratio (%) relative to each of the activity signal peaks.

Figure 6:
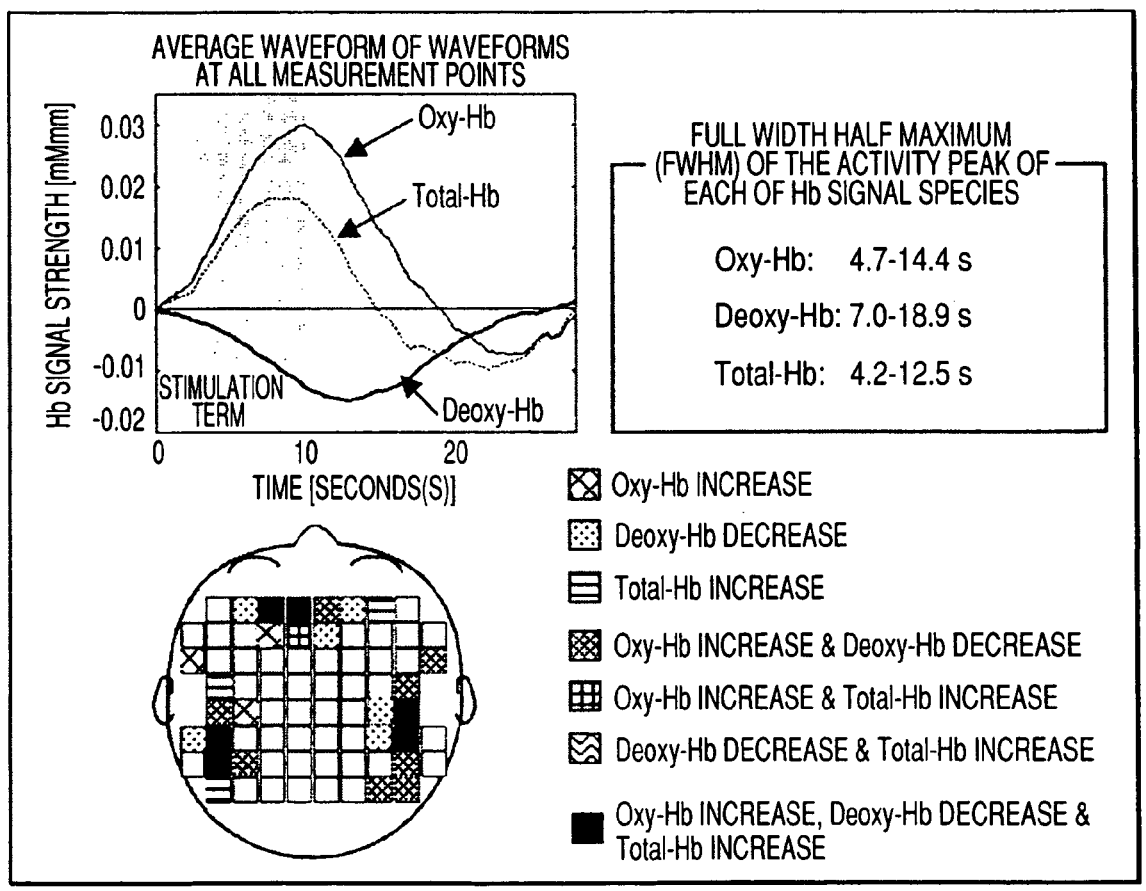
FIG. 6 is a view showing the average waveform of waveforms at all measurement sites about three species of oxy-Hb signal, deoxy-Hb signal and total-Hb signal species, the full width half maximum of an activity peak of each of the Hb signal species, and a screen wherein a situation of brain activity that is the result of a test of the Hb signal species is displayed.

The above-mentioned examples are each a case using the both oxy-Hb signal and deoxy-Hb signal species to evaluate brain activity. However, as illustrated in FIG. 6, the same method as described above can be used in the case of using the three species of oxy-Hb signal, deoxy-Hb signal, and total-Hb signal species. Since the three Hb signal species are used, for example, the number of types of activity of signal species increases from three to seven. When attention is paid to sites where all of the three Hb signal species are active, it can be understood that sites of brain activity are more localized. It can be considered that all sites where all of an increase in the oxy-Hb signal species, a decrease in the deoxy-Hb signal species, and an increase in the total-Hb signal species are observed show typical brain activity that is theoretically expected. In other words, by inflow of arterial blood, the oxy-Hb signal species and the total-Hb signal species are increased. Further the flow rate of the blood becomes larger than the consumption rate of oxygen; thus, the deoxy-Hb signal species is decreased. Other change patterns of the Hb species are, for example, that in the case that the oxy-Hb signal species and the total-Hb signal species are increased but the deoxy-Hb signal species is not decreased in some sites, it is suggested that arterial blood is supplied but a rise in the flow rate of the blood is small and thus these sites are probably out of the center of activity sites. Conversely, in the case that only the deoxy-Hb signal species is decreased but the oxy-Hb signal species and the total-Hb signal species are not increased in some sites, it is presumed that the supply of arterial blood is mainly attained by a rise in the flow rate of the blood and the total amount of blood is hardly increased. It is suggested that these sites are also probably out of the center of brain activity. From these change patterns of the Hb signal species, the situation of brain blood circulation, such as the flexibility of blood vessels therein, may be guessed.

In FIGS. 4 to 6, the average waveform of each of the Hb signal species at all measurement points is shown as an example. However, the waveform of the Hb signal species used to set a time window for an activity period is not necessarily the average value of waveforms at all measurement points. For example, the following can be used: the waveform of the Hb signal species at measurement points which are most active; a standard brain activity waveform which is theoretically obtained (i.e., a template waveform); the average waveform of waveforms at sites to which attention is paid; or a standard activity waveform prepared from past brain activity signals of each of subjects. In the case that Hb signal species waveforms are obtained from each of subjects and the obtained waveforms are used for analysis, difference between individuals' Hb signal waveforms is canceled. Thus, the case is useful for detecting brain activity with a higher precision.

Figure 7:
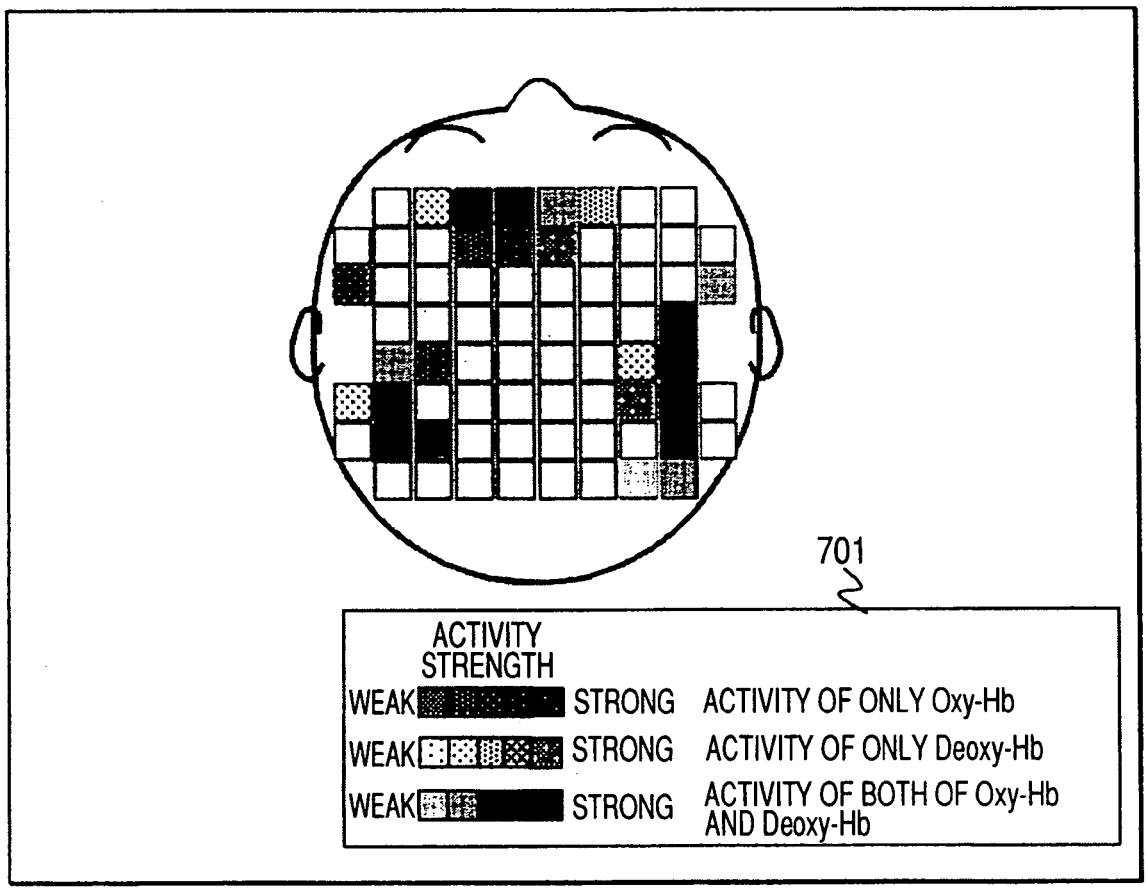
FIG. 7 is a view showing an example wherein only an oxy-Hb signal species, only a deoxy-Hb signal species, and a combination of both of them, which each show brain activity, are each displayed as a color or light and darkness that is stepwise varied in accordance with the activity strength thereof.
Figure 8:
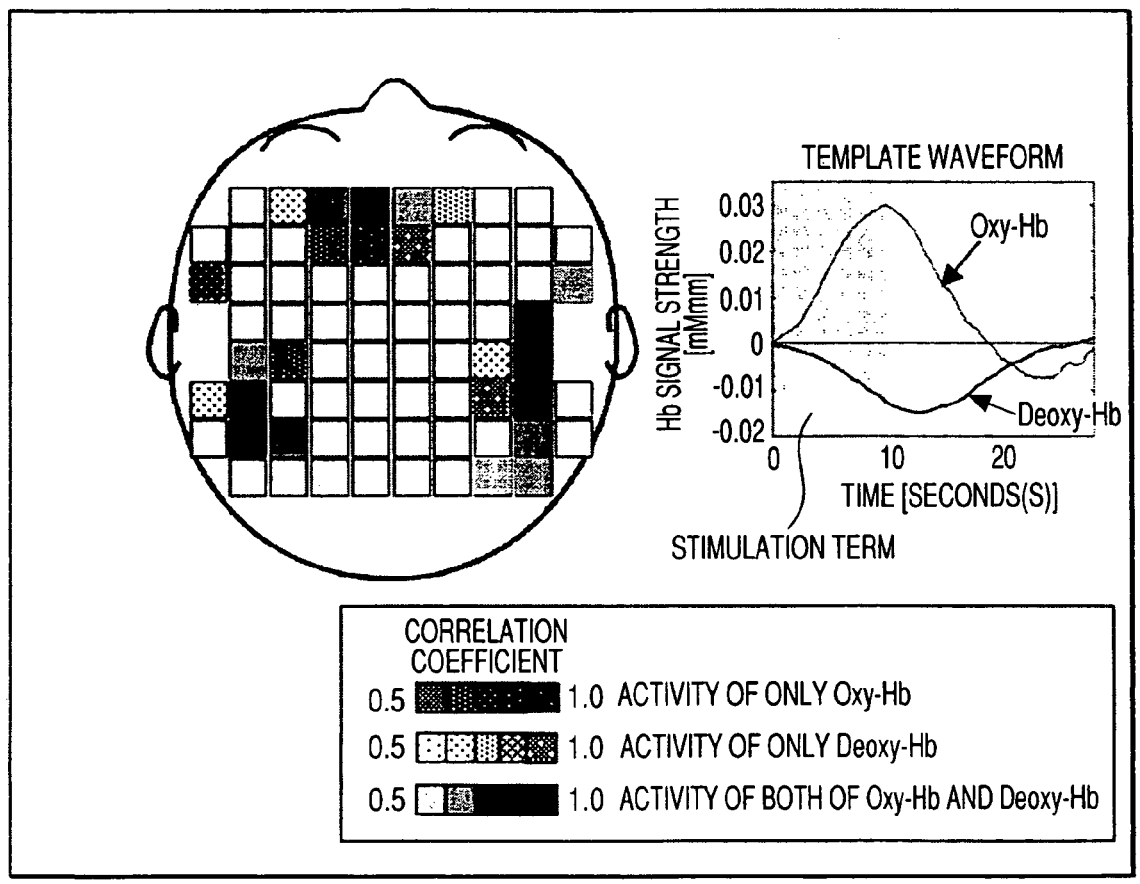
FIG. 8 is a view showing an example wherein only an oxy-Hb signal species, only a deoxy-Hb signal species, and a combination of both of the species, which each show brain activity, are each displayed as a color or light and darkness that is stepwise varied in accordance with a correlation coefficient thereof with some template waveform.

In each of FIGS. 4 to 6, the significance of signal (or brain) activity is statistically tested by use of some threshold, and then the result of the test is classified into "0 or "1". FIG. 7 shows an example wherein activity strength at measurement points wherein activity is exhibited is stepwise indicated. Examples of the activity strength include the average (nM·mm) of signal strengths in an activity period, the maximum value (minimum value) of activity strengths, and t value, F value and p value, which are each a statistical value. In the case that some activity waveform template is used, an index representing the similarity to the template, such as a correlation coefficient to the template, may be used. In the example shown in FIG. 7, first, whether or not each of Hb signal species shows activity as shown in FIGS. 4 to 6 is statistically tested. Thereafter, the average of signal strengths in the activity period of each of the signal species is displayed in a color bar 701. When the oxy-Hb signal species and the deoxy-Hb signal species show activity independently of each other, it is advisable to display the average signal strengths of the individual species as light and darkness of different colors, or the like. When both of the oxy-Hb signal species and the deoxy-Hb signal species show activity, the light and darkness of a color different from the colors when the individual species show activity independently of each other is used to display the sum of the oxy-Hb signal species strength and the deoxy-Hb signal species strength, or the average value of the strengths. Alternatively, in the case that the oxy-Hb signal species strength and the deoxy-Hb signal species strength are extremely different from each other, or in some other case, it is useful to standardize the oxy-Hb signal species strength and the deoxy-Hb signal species strength into the same level, and then calculate the signal strength of the combination of the standardized strengths. FIG. 8 shows an example wherein indicated is a correlation coefficient at the time of using, as a template waveform, the average waveform of waveforms at all measurement points, an activity waveform at the measurement point which is most active, or a standard brain activity waveform which is theoretically obtained. In this example, it is tested whether or not individual Hb signal species each show activity by use of some threshold value in the same way as shown in FIG. 7, and then the correlation coefficients thereof are indicated by light and darkness of different colors. When plural ones out of the Hb signal species (such as the oxy-Hb signal species and the deoxy-Hb signal species) show significant activity, the average of correlation coefficients thereof or the like is indicated. In this way, the classification based on whether the activity of combination of plural ones out of the Hb signal species is significant or not is indicated, and additionally the strength of the activity may be stepwise indicated. In this case, a more localized activity site can easily be detected.

Figure 9:
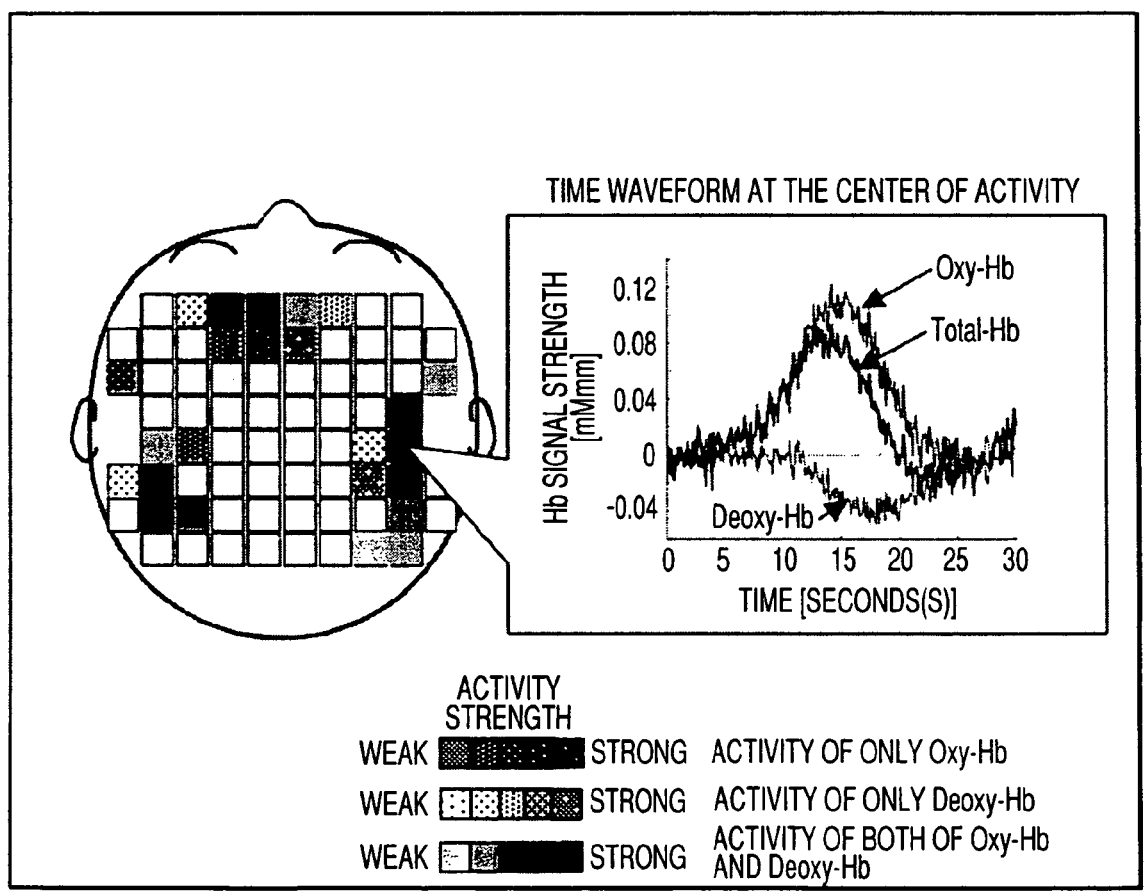
FIG. 9 is a view showing a screen displaying a brain activity map and a time change in each Hb signal species at the measurement site of the activity center of the Hb signal species.
Figure 10:
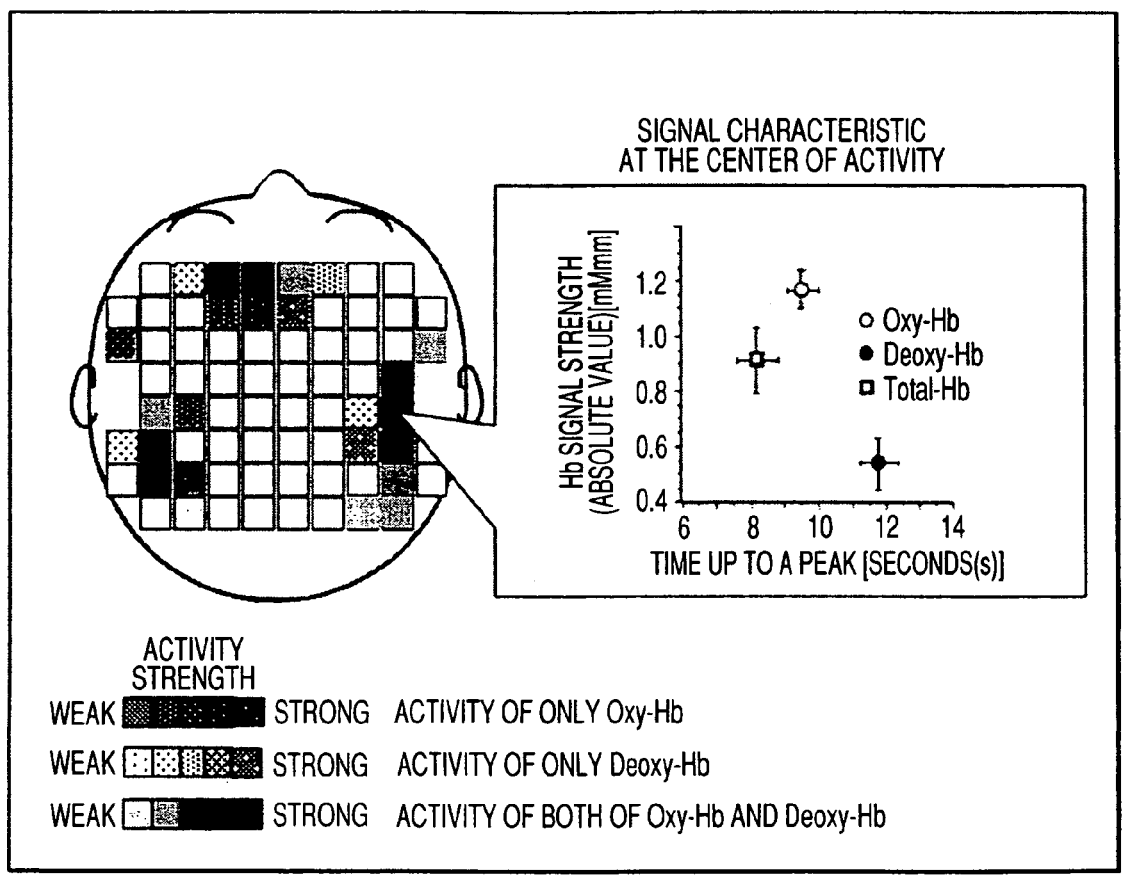
FIG. 10 is a view showing a graph displaying a brain activity map and a graph wherein the strength of each Hb signal species at the measurement site of the activity center of the Hb signal species is taken as its vertical axis and the time up to arrival at an activity peak of the Hb signal species is taken as its transverse axis.

It is effective for investigating brain activity in detail to detect brain activity sites by any one of the above-mentioned methods and subsequently display details of the activity at each of the activity sites. FIG. 9 shows an example wherein about each of oxy-Hb signal and deoxy-Hb signal species, activity sites thereof are shown and further the measurement point which is most active out of the sites is selected and the time waveform of the Hb signal species at the measurement point is indicated. To indicate a time change in each of actual Hb signal species in such a way is useful for ascertaining that brain activity is not any artifact or evaluating the activity pattern thereof. FIG. 10 is a graph wherein a peak value of each Hb signal species or the average value of activity periods thereof is taken as its vertical axis and a time required up to arrival at the activity peak is taken as its transverse axis, the graph being useful for investigating brain activity in detail. Error bars therein each show a standard deviation, a standard error, a confidence interval, or the like. From this graph indicator, it can be understood which of the Hb signal species is largest in strength or which of the Hb signal species reaches a signal strength peak most rapidly. The pattern of this graph is useful for evaluating the situation of blood circulation which accompanies brain activity. According to a precedent finding, the following is known about change in Hb signal species which accompanies brain activity: an increase in the total-Hb signal species first reaches a peak; then, an increase in the oxy-Hb signal species reaches a peak; and finally a decrease in the deoxy-Hb signal species reaches a peak. When this graph is used, it is possible to decide, with ease, whether or not the measured change is consistent with the known typical pattern. Accordingly, a function of displaying whether to not the measured change is consistent with the typical pattern to users can be added to the device of the invention. In FIGS. 9 and 10 is an example wherein only one measurement point is selected from all measurement points and then the time waveform at this point is displayed. However, time waveforms at plural ones out of all measurement points can be displayed. For example, a method of setting plural regions, such as the frontal region and the temporal regions, and then selecting the measurement site wherein activity strength is largest in each of the regions is also effective.

The above examples are examples for supporting the evaluation of brain activity; in the same manner, diagnosis of brain function or diagnosis of brain blood circulation can be supported. For example, as illustrated in FIG. 2, brain activity is analyzed and displayed at intervals of time windows of 2.5 seconds from the start of a stimulation. In this case, the spatial spread of activity of each Hb signal species and the time window when the activity arrives at a peak are easily understood (FIG. 2). The oxy-Hb signal species first increases, and after 2.6 to 5.0 seconds from the start of the stimulation, activity sites begin to make their appearance. In a period from 7.6 to 12.5 seconds therefrom, the number of the measurement points which show activity becomes largest. On the other hand, a decrease in the deoxy-Hb signal species is delayed, and after 7.6 to 10.0 seconds from the start of the stimulation, activity sites begin to make their appearance. In a period from 10.1 to 15.0 seconds therefrom, the number of the measurement points which show activity becomes largest. This pattern would be one typical activity pattern, which depends somewhat on individual persons. For example, in the case that a region where an increase in the oxy-Hb signal species, which should first be observed, is narrow or the strength of activity is small, the case means that arterial blood supply which accompanies brain activity is small. Thus, it is suggested that the flexibility of the blood vessels is probably low. Alternatively, in the case that an increase in the deoxy-Hb signal species is first observed and behind time an increase in the oxy-Hb signal species is observed, arterial blood supply tends to be slow in the same manner. Thus, it is suggested that the flexibility of the blood vessels is probably low. In the case that a decrease in the deoxy-Hb signal species is not observed or is small, it can be considered that an increase in the flow rate of blood is not remarkable. Thus, it is suggested that the flexibility of the blood vessels is probably high or the flow of blood is probably lacking. Alternatively, it is suggested that consumption of oxygen balancing the arterial blood supply may advance. In the case that a change pattern which is different from these patterns and is remarkably apart from physiological changes that are expected is observed, it is feared that no brain activity signal can be measured. Thus, a function of displaying an error message is also useful.

What is claimed is:

1. A living body light measuring device, comprising:
   plural light-radiating means from which light is radiated to a head of a subject;
   plural light-receiving means for detecting light which is transmitted through the head of the subject after radiation from the light-radiating means;
   a calculator for calculating a change of concentration of oxidized hemoglobin and a change of concentration of deoxidized hemoglobin in the head of the subject at a measurement point comprising a pair of each of the plural light-radiating means and corresponding ones of the light-receiving means, wherein the measurement point includes a signal detected by the light-receiving means
   a display for displaying the calculations obtained from the calculator,
   wherein the calculator decides whether the oxidized hemoglobin concentration change and the deoxidized hemoglobin concentration change are statistically significant at each of the measurement points, and
   the display displays the decisions regarding the individual measurement points, wherein the display displays the decision lined up in accordance with measuring times.

2. The living body light measuring device according to claim 1, wherein the display displays at least one of color, and pattern, or lightness or darkness of color which is varied on the basis of the decision.

3. The living body light measuring device according to claim 1, wherein the display displays the decision varied in accordance with at least one of the significance of matter that the oxidized hemoglobin concentration change, the significance of matter that the deoxidized hemoglobin concentration change, and the significance of the matter that each of the oxidized hemoglobin concentration change and the deoxidized hemoglobin concentration change.

4. The living body light measuring device according to claim 1, wherein the calculator decides whether the oxidized hemoglobin concentration change and the deoxidized hemoglobin concentration change are each significant on the basis of statistical analysis.

5. The living body light measuring device according to claim 4, wherein; in the statistical analysis, any one of a parametric test and a nonparametric test is used.

6. The living body light measuring device according to claim 1, which further comprises a setting-up section for setting up the decision made by the calculator.

7. The living body light measuring device according to claim 1, wherein the calculator decides whether the oxidized hemoglobin concentration change and the deoxidized hemoglobin concentration change are each significant on the basis of similarity of a brain activity waveform at each of the measurement points to a predetermined template waveform.

8. The living body light measuring device according to claim 7, wherein the template waveform is any one of an average waveform of brain activity waveforms at all of the measurement points, a brain activity waveform at the measurement point where the brain works most actively, and a standard brain activity waveform.

9. The living body light measuring device according to claim 1, which further comprises a setting-up section in which an activity period is inputted for each of oxidized hemoglobin and deoxidized hemoglobin,
   wherein the calculator decides whether the oxidized hemoglobin concentration change and the deoxidized hemoglobin concentration change are significant in the respective activity periods inputted from the setting-up section.

10. The living body light measuring device according to claim 1, wherein the calculator calculates a peak time of brain activity for each of oxidized hemoglobin and deoxidized hemoglobin,
   the device further comprising a setting-up section for setting up a brain activity change period, the center of the change period being the peak time, and, on the basis of the brain activity change during the change period, the calculator deciding whether the oxidized hemoglobin concentration change and the deoxidized hemoglobin concentration change are each significant during the said change period.

11. The living body light measuring device according to claim 10, wherein the peak time is calculated from any one of an average waveform of brain activity waveforms at all of the measurement points, a brain activity waveform at the measurement point where the brain works most actively, a standard brain activity waveform, an average waveform of brain activity waveforms at sites to be measured, and a standard brain activity waveform prepared by past brain activity signals of the subject.

12. The living body light measuring device according to claim 1, wherein the display displays the decision at the measurement points stepwise based on the significances of oxidized hemoglobin and deoxidized hemoglobin.

13. The living body light measuring device according to claim 1, wherein the display displays a brain activity waveform at the measurement point where the oxidized hemoglobin concentration change or the deoxidized hemoglobin concentration change is most significant.

14. The living body light measuring device according to claim 1, wherein the calculator decides whether the oxidized hemoglobin concentration change, the deoxidized hemoglobin concentration change, and a change in the concentration of all hemoglobins are each significant at each statistically of the measurement points.

15. The living body light measuring device according to claim 1, wherein the measurement point is substantially at a middle point between the pair of the light-radiating means and the light-receiving means.

16. The living body light measuring device according to claim 1, wherein the plural light-radiating means and the plural light-receiving means are alternately arranged in a lattice form.

* * * * *